United States Patent

Benazzi et al.

Patent Number: 6,096,939
Date of Patent: Aug. 1, 2000

[54] ALIPHATIC ALKYLATION UTILIZING A LIQUID CATALYST

[75] Inventors: Eric Benazzi, Montesson; Jean-Francois Joly, Lyons; Nathalie Ferrer, Chatou; Bernard Torck, Boulogne Sur Seine, all of France

[73] Assignee: Institut Francais du Petrole, France

[21] Appl. No.: 09/115,546

[22] Filed: Jul. 15, 1998

Related U.S. Application Data

[62] Division of application No. 08/684,441, Jan. 19, 1996, Pat. No. 5,849,978.

[30] Foreign Application Priority Data

Jul. 20, 1995 [FR] France ................. 95 08931

[51] Int. Cl.$^7$ ................. C07C 2/62
[52] U.S. Cl. ................. 585/730; 585/732; 585/709; 585/721
[58] Field of Search ................. 585/730, 732, 585/709, 721

[56] References Cited

U.S. PATENT DOCUMENTS

| | | | |
|---|---|---|---|
| 3,778,489 | 12/1973 | Parker et al. | 585/722 |
| 3,795,712 | 3/1974 | Torck et al. | 585/455 |
| 3,922,319 | 11/1975 | Brockington | 585/731 |
| 4,800,186 | 1/1989 | Tasset | 502/33 |
| 5,196,628 | 3/1993 | Del Rossi et al. | 585/725 |
| 5,284,993 | 2/1994 | Eastman | 585/842 |
| 5,849,978 | 12/1998 | Benazzi et al. | 585/730 |

FOREIGN PATENT DOCUMENTS

93/00316  1/1973  WIPO .

*Primary Examiner*—Walter D. Griffin
*Assistant Examiner*—Nadine Preisch
*Attorney, Agent, or Firm*—Millen, White, Zelano & Branigan, P.C.

[57] ABSTRACT

The invention concerns the catalytic alkylation of at least one isoparaffin selected from the group formed by isobutane and isopentane in the presence of at least one olefin containing 3 to 6 carbon atoms per molecule, using a catalyst comprising 40% to 99% by weight of an acid selected from acids with formula R—$SO_3H$ where R is fluorine or an alkyl group or a fluorinated alkyl group, R preferably being F or $CF_3$, and more preferably $CF_3$, and 1% to 60% by weight of a solvent selected from the group formed by sulpholane, dimethylsulphoxide and dioxanes, preferably sulpholane.

5 Claims, No Drawings

ALIPHATIC ALKYLATION UTILIZING A LIQUID CATALYST

This application is a divisional application of Ser. No. 08/684,441, filed Jan. 19, 1996, now U.S. Pat No. 5,849,978.

The present invention concerns a catalyst comprising 40% to 99% by weight of an acid selected from acids with formula R—SO$_3$H where R is fluorine or an alkyl group or a fluorinated alkyl group, R preferably being F or CF$_3$, more preferably CF$_3$, and 1% to 60% by weight of a solvent selected from the group formed by sulpholane, dioxanes and dimethylsulphoxide, preferably sulpholane, and more particularly its use for the aliphatic alkylation, i.e., catalytic alkylation of a C$_4$–C$_5$ isoparaffin, i.e., containing 4 or 5 carbon atoms per molecule (isobutane and/or isopentane) using at least one olefin containing 3 to 6 carbon atoms per molecule (i.e., a C$_3$–C6 olefin), to obtain paraffinic compounds with a high degree of branching and a high octane number.

A large number of liquid or solid acid catalysts are known for use in carrying out the aliphatic alkylation of isoparaffin(s) such as isobutane or isopentane using at least one olefin such as propylene, 1- and 2-butenes or isobutene. The catalysts which are most frequently used in the industry are liquid catalysts, namely pure sulphuric acid and hydrofluoric acid, used alone or mixed with Lewis acids such as boron trifluoride. These processes suffer considerable disadvantages: hydrofluoric acid because of its toxicity and high volatility; and sulphuric acid because of its high consumption of catalyst, necessitating costly reprocessing.

United States patent U.S. Pat. No. 3,795,712 describes, in order to catalyse the alkylation of aromatic compounds by at least one olefin or the aliphatic alkylation of isobutane by at least one olefin or the oligomerisation or polymerisation of olefins, catalytic compositions comprising a Lewis or Brönsted acid and a sulphone with formula R-SO$_2$—R', where R and R' are each and separately a monovalent radical comprising 1 to 8 carbon atoms per molecule, or together form a divalent radical containing 3 to 12 carbon atoms per molecule, optionally in an inert hydrocarbon solvent, the acid concentration being in the range 10$^{-5}$ moles per liter of sulphone to 5 moles per liter of sulphone, i.e., in the range 0.00012% to 37% by weight of acid when the acid is trifluoromethanesulphonic acid and the sulphone is sulpholane.

International patent application PCT WO 93/00316 describes catalytic compositions for aliphatic alkylation comprising 10% to 90% by weight of hydrofluoric acid or sulphonic acid substituted with at least one halogen and 10% to 90% by weight of a solvent with a donor number of less than 40 in the absence of intentionaly added metal halide. The long list of such solvents includes sulpholane (tetramethylene sulphone) and dimethylsulphoxide.

The catalyst which is used in accordance with the present invention constitutes an improvement over the catalytic compositions described in U.S. Pat. No. 3,795,712 and WO 93/00316 used for aliphatic alkylation.

The present invention concerns the alkylation of a C$_4$–C$_5$ isoparaffin by at least one C$_3$–C$_6$ olefin using a catalyst comprising 40% to 99% by weight of an acid selected from acids with formula R—SO$_3$H where R is fluorine or an alkyl group or a fluorinated alkyl group (partially or completely fluorinated), R preferably being F or CF$_3$, more preferably CF$_3$, and 1% to 60% by weight of a solvent selected from the group formed by sulpholane (trade name for tetrahydrothiophene dioxide), dimethylsulphoxide (also known as dimethylsulphinone) and dioxanes (1,2-dioxane and 1,4-dioxane), preferably sulpholane. The catalyst thus preferably comprises fluorosulphonic acid HSO$_3$H or trifluoromethanesulphonic acid CF$_3$SO$_3$H, and a solvent. More preferably, the catalyst comprises trifluoromethanesulphonic acid CF$_3$SO$_3$H and a solvent. The catalyst comprises (in weight %) 40% to 99% by weight, preferably 45% to 98% by weight, more preferably 55% to 97% by weight of acid and 1% to 60% by weight, preferably 2% to 55% by weight, more preferably 3% to 45% by weight of solvent.

The acid is generally 95% to 100% by weight pure, preferably 98% to 100% by weight pure, the most usual complement to 100% being constituted by water.

The solvent is generally miscible with the acid and not miscible with the hydrocarbon phase. The basicity of the solvent must be as low as possible in order not to reduce the protonic activity of the acid with which it is mixed.

The catalyst as used in accordance with the invention is thus a liquid phase catalyst.

One advantage of the catalyst used in accordance with the invention over 97% to 99% pure sulphuric acid which is currently used in alkylation units is that it has an equal or higher acidity and a far lower oxidising character, since the acid comprised in the catalyst has a far lower oxidising character than sulphuric acid. A further advantage of the catalyst used in accordance with the invention over trifluoromethanesulphonic acid is a limit to the undesirable passage into hydrocarbon solution of the acid in the catalyst in the form of compounds known as alkyl triflates when the acid is trifluoromethanesulphonic acid.

A still further advantage of the catalyst used in accordance with the invention is the quality of the alkylate obtained, which has a lower sulphur content than when sulphuric acid or trifluoromethanesulphonic acid is used.

A yet still further advantage of the catalyst used in accordance with the present invention is that the use of this catalyst leads to a reduction in catalyst consumption and thus to a reduction in the operating costs of alkylation units.

The preparation process for the catalyst of the invention generally comprises at least two steps. The first step consists of purifying the solvent, for example by distillation, then in a second step the acid and solvent are mixed in the desired proportions.

The invention thus concerns the use of the catalyst for the catalytic alkylation of at least one isoparaffin selected from the group formed by isobutane and isopentane (i.e., isobutane and/or isopentane: isobutane, or isopentane, or isobutane and isopentane) in the presence of at least one olefin containing 3 to 6 carbon atoms per molecule.

The catalyst used in accordance with the present invention is employed in a process which effects the alkylation of an isoparaffin with at least one olefin under optimum conditions. In particular, since the reaction is highly exothermic (about 83.6 kJ/mol of butene transformed if the olefin is butene and the isoparaffin is isobutane), using the catalyst in accordance with the present invention can achieve good homogeneity of temperature and reactant concentration. In particular, any technique which is known to the skilled person in which the apparatus comprises at least one reactor and at least one settler can use the catalyst of the present invention.

Existing processes for the production of hydrocarbons by alkylation of isobutane using olefins generally employ processes in which the reaction medium is two-phase (either sulphuric acid or hydrofluoric acid for existing commercial processes). The continuous phase is either the acid phase or the hydrocarbon phase. In general, the continuous phase is the acid phase; the acid catalyst constitutes a liquid phase which is brought into contact with the liquid isobutane-olefin(s) mixture to form an emulsion and the acid/hydrocarbon volume ratio is greater than 1. As an example, when using sulphuric acid in the Stratco process (L. F. Albright, Chem. Eng., Aug. 15, 1966, p 143 and L. F. Albright, Oil & Gas Journal, Nov. 12, 1990), which is the most widely used process, the emulsion is created at one extremity of a horizontal reactor by a turbine which is supplied with the feed and recycled acid. It is also possible for the hydrocarbon phase to be the continuous phase (see, for example, International patent application PCT WO 95/04.019).

The processes used in the present invention are generally processes where the reaction medium is two-phase, comprising an acid phase and a hydrocarbon phase. The continuous phase is either the acid phase or the hydrocarbon phase.

The reaction temperature is generally below +20° C., preferably below +15C. and more preferably in the range +5C. to −5C. The pressure in the reaction zone is sufficient to maintain the hydrocarbons in the liquid state in that zone.

The hourly space velocity, expressed as the weight of olefin introduced per unit weight of catalyst per hour (wwh), is in the range $0.001\ h^{-1}$ to $10\ h^{-1}$, preferably in the range $0.002\ h^{-1}$ to $2\ h^{-1}$. In all cases, the mixture formed in the reaction zone is under pressure and temperature conditions such that the hydrocarbon mixture remains liquid.

In order to limit secondary reactions, an excess of isoparaffin(s) with respect to olefin(s) can be used. As an example, in the case of alkylation of isobutane with a butene, the isobutane can be introduced pure into the feed or in the form of a mixture of butanes containing, for example, at least 40% of isobutane.

Further, a butene can be introduced pure or as a mixture of butene isomers. In all cases, the isobutane/butene molar ratio in the feed is generally in the range 1 to 100, preferably in the range 3 to 50 and more preferably in the range 5 to 15.

When the nature of the catalyst and the reaction conditions are carefully selected (in particular the temperature), the catalyst of the invention can produce alkylation products of at least one isoparaffin and at least one olefin which are important as motor fuels and petrol constituents and which comprise, for example, at least 60 mole % of paraffins containing 8 carbon atoms per molecule and less than 1 mole % of unsaturated compounds, the paraffins containing 8 carbon atoms per molecule comprising 70 to 98 mole % of trimethylpentanes.

The following examples illustrate the invention without in any way limiting its scope.

EXAMPLE 1

Preparation of Catalyst 1 in Accordance with the Invention 100 g of an acid phase in accordance with the invention was prepared by mixing 80 g of 98% pure trifluoromethanesulphonic acid with 20 g of sulpholane which had been vacuum distilled. The prepared acid phase thus contained 20% by weight of sulpholane and 80% by weight of 98% pure trifluoromethanesulphonic acid.

Alkylation of Isobutane by 2-Butene Using Catalyst 1 With a Continuous Hydrocarbon Phase 25 g of catalyst 1 prepared as described above was introduced into a glass reactor with a volume of 500 ml which had been purged with argon. The reactor containing the catalyst was closed and cooled to a temperature of −1 C.

100 ml of isobutane was then introduced into the reactor and the reaction medium was stirred at a rate of 2000 rotations per minute. The reactor was cooled to −1 C. by circulating a colder liquid in the double envelope with which it was equipped. A rotatable axle provided with a turbine was used for stirring.

After 30 minutes of homogenisation, 190 g of a mixture constituted by 10% by weight of 2-butene and 90% by weight of isobutane was regularly added over a total period of 5 hours, the reactor temperature being maintained at −1 C. for the whole of the injection period.

After reaction and settling, the hydrocarbon phase was extracted from the reactor, isolated then analysed by gas chromatography; its composition by weight is shown in Table 1.

EXAMPLE 2

Preparation of Catalyst 2. Not in Accordance With the Invention

The catalyst used in this example was 98% pure trifluoromethanesulphonic acid, with no addition of solvent.

Alkylation of Isobutane by 2-Butene With Catalyst 2 With a Continuous Hydrocarbon Phase The test for the catalytic alkylation of isobutane by 2-butene was repeated under the same experimental conditions as those used for Example 1, and the same analyses were carried out. The only difference was that in the present example, 20 g of acid was introduced into the reactor. The results are shown in Table 1.

EXAMPLE 3

Preparation of Catalyst 3 in Accordance With the Invention 100 g of an acid phase in accordance with the invention was prepared by mixing 80 g of 100% pure trifluoromethanesulphonic acid with 20 g of sulpholane which had been vacuum distilled. The 80 g of 100% pure trifluoromethanesulphonic acid had been taken from a preparation of 100 g of trifluoromethanesulphonic acid obtained by mixing 76.13 g of 98% trifluoromethanesulphonic acid with 23.87 g of trifluoromethanesulphonic acid anhydride $(CF_3SO_2)_2O$. The prepared acid phase thus contained 20% by weight of sulpholane and 80% by weight of 100% by weight concentrated trifluoromethanesulphonic acid $(CF_3SO_3H)$.

Alkylation of Isobutane by 2-Butene Using Catalyst 3 With A Continuous Hydrocarbon Phase 25 g of catalyst 3 prepared as described above was introduced into a glass reactor with a volume of 500 ml which had been purged with argon. The reactor containing the catalyst was closed and cooled to a temperature of −1 C.

100 ml of isobutane was then introduced into the reactor and the reaction medium was stirred at a rate of 2000 rotations per minute. The reactor was cooled to −1 C. by circulating a colder liquid in the double envelope with which it was equipped. A rotatable axle provided with a turbine was used for stirring.

After 30 minutes of homogenisation, 190 g of a mixture constituted by 10% by weight of 2-butene and 90% by weight of isobutane was regularly added over a total period of 5 hours, the reactor temperature being maintained at −1 C. for the whole of the injection period.

After reaction and settling, the hydrocarbon phase was extracted from the reactor, isolated then analysed by gas chromatography; its composition by weight is shown in Table 1.

EXAMPLE 4

Preparation of Catalyst 4. Not in Accordance With the Invention 100 g of an acid phase in accordance with the invention was prepared by mixing 10 g of 100% pure trifluoromethanesulphonic acid with 90 g of sulpholane which had been vacuum distilled. The 10 g of 100% pure trifluoromethanesulphonic acid had been taken from 100 g of 100% pure trifluoromethanesulphonic acid prepared by mixing 76.13 g of 98% trifluoromethanesulphonic acid with 23.87 g of trifluoromethanesulphonic acid anhydride $(CF_3SO_2)_2O$. The prepared acid phase thus contained 90% by weight of sulpholane and 10% by weight of 100% by weight pure trifluoromethanesulphonic acid $(CF_3SO_3H)$.

Alkylation of Isobutane by 2-Butene Using Catalyst 4 With A Continuous Hydrocarbon Phase 25 g of catalyst 4 prepared as described above was introduced into a glass reactor with a volume of 500 ml which had been purged with argon. The reactor containing the catalyst was closed and cooled to a temperature of –1 C.

100 ml of isobutane was then introduced into the reactor and the reaction medium was stirred at a rate of 2000 rotations per minute. The reactor was cooled to –1 C by circulating a colder liquid in the double envelope with which it was equipped. A rotatable axle provided with a turbine was used for stirring.

After 30 minutes of homogenisation, 190 g of a mixture constituted by 10% by weight of 2-butene and 90% by weight of isobutane was regularly added over a total period of 5 hours, the reactor temperature being maintained at –1 C for the whole of the injection period.

After reaction and settling, the hydrocarbon phase was extracted from the reactor, isolated then analysed by gas chromatography; its composition by weight is shown in Table 1.

It should be noted that in this example, in contrast to the preceding examples, conversion of 2-butene was not complete and was about 75%.

TABLE 1

Comparison of catalysts 1, 2, 3 and 4

| Alkylate composition (weight %) | Example 1, catalyst 1 in accordance with the invention | Example 2, catalyst 2 not in accordance with the invention | Example 3, catalyst 3 in accordance with the invention | Example 4, catalyst 4 not in accordance with the invention |
|---|---|---|---|---|
| $C_5$–$C_7$ | 2.3 | 1.5 | 2.6 | 6.7 |
| $C_8$ | 92.6 | 84.2 | 93.7 | 57.7 |
| $C_9^+$ | 5.1 | 14.3 | 3.7 | 35.6 |

This table shows the importance of operating with the catalysts of the invention, i.e., those comprising an acid phase comprising trifluoromethanesulphonic acid and an aprotic organic solvent with low basicity. The catalysts of the invention have better selectivities than those which are not in accordance with the invention.

The use of catalyst 2 which was not in accordance with the invention produced a fuming alkylate, i.e., containing trifluoromethanesulphonic acid $CF_3SO_3H$, and as a consequence that alkylate contained far more alkyl triflates than the alkylates obtained with catalysts 1 and 3 which did not exhibit this characteristic. With catalyst 4 which was not in accordance with the invention, the lack of accordance of the catalyst resulted in incomplete conversion of the olefin and above all in a very poor alkylate quality (too much heavy $C_9^+$).

EXAMPLE 5

Preparation of Catalyst 5. Not in Accordance With the Invention 100 g of an acid phase which was not in accordance with the invention was prepared by mixing 80 g of 100% pure trifluoromethanesulphonic acid with 20 g of triethylamine which had a donor number of 30.5 (close to the donor number of dimethylsulphoxide of 29.8).

Alkylation of Isobutane by 2-Butene Using Catalyst 5 With A Continuous Hydrocarbon Phase 25 g of catalyst 5 prepared as described above was introduced into a glass reactor with a volume of 500 ml which had been purged with argon. The reactor containing the catalyst was closed and cooled to a temperature of –1 C.

100 ml of isobutane was then introduced into the reactor and the reaction medium was stirred at a rate of 2000 rotations per minute. The reactor was cooled to –1 C. by circulating a colder liquid in the double envelope with which it was equipped. A rotatable axle provided with a turbine was used for stirring.

After 30 minutes of homogenisation, 190 g of a mixture constituted by 10% by weight of 2-butene and 90% by weight of isobutane was regularly added over a total period of 5 hours, the reactor temperature being maintained at –1 C for the whole of the injection period.

Conversion of 2-butene was very low, which was certainly due to insufficient acidity of the solvent.

EXAMPLE 6

Preparation of Catalyst 6. Not in Accordance With the Invention 100 g of an acid phase which was not in accordance with the invention was prepared by mixing 80 g of 100% pure trifluoromethanesulphonic acid with 20 g of acetone which had a donor number of 17.0 (close to the donor number of sulpholane of 14.8). A red mixture was obtained, signifying a reaction between the acetone and the trifluoromethanesulphonic acid.

Under these conditions, an alkylation test carried out as described in the above examples did not lead to the formation of an alkylate.

What is claimed is:

1. A process for the catalytic alkylation of at least one isoparaffin selected from the group consisting of isobutane and isopentane comprising reacting said at least one isoparaffin with at least one olefin containing 3 to 6 carbon atoms per molecule in a reaction zone in the presence of a catalyst comprising 40% to 90% by weight of trifluoromethane sulfonic acid and 10% to 60% by weight of sulpholane.

2. A process according to claim 1, in which the purity of the acid is in the range of 95% to 100% by weight.

3. A process according to claim 1, in which the reaction temperature is below +20° C., the pressure in the reaction zone is sufficient to maintain all hydrocarbons in the liquid state in said zone and the reaction zone contains a two-phase reaction medium having a continuous phase and a dispersed phase.

4. A process according to claim 3, in which the continuous phase comprises an acid phase.

5. A process according to claim 3, in which the continuous phase comprises a hydrocarbon phase.

* * * * *